(12) United States Patent
Schaefer (10) Patent No.: US 9,739,790 B2
(45) Date of Patent: Aug. 22, 2017

(54) CARDIOVASCULAR DISEASE RISK ASSESSMENT

(71) Applicant: Boston Heart Diagnostic Corporation, Framingham, MA (US)

(72) Inventor: Ernst J. Schaefer, Natick, MA (US)

(73) Assignee: Boston Heart Diagnostic Corporation, Framingham, MA (US)

( * ) Notice: Subject to any disclaimer, the term of this patent is extended or adjusted under 35 U.S.C. 154(b) by 0 days.

(21) Appl. No.: 14/943,775

(22) Filed: Nov. 17, 2015

(65) Prior Publication Data

US 2016/0139160 A1   May 19, 2016

Related U.S. Application Data

(60) Provisional application No. 62/080,833, filed on Nov. 17, 2014.

(51) Int. Cl.
*G01N 33/92* (2006.01)
*G06F 19/24* (2011.01)

(52) U.S. Cl.
CPC ............ *G01N 33/92* (2013.01); *G06F 19/24* (2013.01); *G01N 2333/775* (2013.01); *G01N 2405/00* (2013.01); *G01N 2800/32* (2013.01); *G01N 2800/50* (2013.01)

(58) Field of Classification Search
None
See application file for complete search history.

(56) References Cited

U.S. PATENT DOCUMENTS

| | | |
|---|---|---|
| 3,703,591 A | 11/1972 | Bucolo |
| 4,245,041 A | 1/1981 | Denney |
| 4,330,299 A | 5/1982 | Cerami |
| 4,495,279 A | 1/1985 | Karpetsky et al. |
| 4,683,195 A | 7/1987 | Mullis et al. |
| 4,683,202 A | 7/1987 | Mullis |
| 4,800,159 A | 1/1989 | Mullis et al. |
| 4,999,289 A | 3/1991 | Akiba et al. |
| 5,223,392 A | 6/1993 | Cohen |
| 5,436,149 A | 7/1995 | Barnes |
| 5,843,663 A | 12/1998 | Stanley et al. |
| 5,849,481 A | 12/1998 | Urdea et al. |
| 5,849,486 A | 12/1998 | Heller et al. |
| 5,851,772 A | 12/1998 | Mirzabekov et al. |
| 5,888,827 A | 3/1999 | Kayahara et al. |
| 5,900,481 A | 5/1999 | Lough et al. |
| 5,919,626 A | 7/1999 | Shi et al. |
| 5,955,351 A | 9/1999 | Gerdes et al. |
| 6,194,164 B1 | 2/2001 | Matsui et al. |
| 6,316,196 B1 | 11/2001 | Morten |
| 6,410,309 B1 | 6/2002 | Barbera-Guillem et al. |
| 6,582,908 B2 | 6/2003 | Fodor et al. |
| 7,417,039 B2 | 8/2008 | Davis |
| 7,435,541 B2 | 10/2008 | Olson et al. |
| 7,608,405 B2 | 10/2009 | Ebinuma et al. |
| 7,659,107 B2 | 2/2010 | Smith et al. |
| 7,700,277 B2 | 4/2010 | Ambrose et al. |
| 7,871,789 B2 | 1/2011 | Yonehara et al. |
| 8,003,795 B2 | 8/2011 | Liu et al. |
| 8,026,345 B2 | 9/2011 | Burghardt et al. |
| 8,093,222 B2 | 1/2012 | Freier et al. |
| 8,470,541 B1 | 6/2013 | Asztalos et al. |
| 8,765,377 B2 | 7/2014 | Schaefer et al. |
| 2002/0087276 A1 | 7/2002 | Otvos |
| 2003/0143223 A1 | 7/2003 | Cabezas et al. |
| 2004/0131658 A1 | 7/2004 | Kaput |
| 2004/0259179 A1 | 12/2004 | Assmann et al. |
| 2005/0054005 A1 | 3/2005 | Ellis et al. |
| 2005/0059581 A1 | 3/2005 | Mantzoros |
| 2005/0239136 A1 | 10/2005 | Hazen et al. |
| 2005/0261558 A1 | 11/2005 | Eaton et al. |
| 2005/0281868 A1 | 12/2005 | Lane |
| 2006/0293225 A1 | 12/2006 | Dialynas et al. |
| 2007/0003600 A1 | 1/2007 | Moore et al. |
| 2007/0015291 A1 | 1/2007 | Smith |
| 2007/0031838 A1 | 2/2007 | Ambrose et al. |
| 2007/0059722 A1 | 3/2007 | Salonen et al. |
| 2007/0196841 A1 | 8/2007 | Ruano et al. |

(Continued)

FOREIGN PATENT DOCUMENTS

| | | |
|---|---|---|
| CN | 103589776 | * 2/2014 |
| EP | 1 186 672 A2 | 3/2002 |

(Continued)

OTHER PUBLICATIONS

Asztalos B. et al. Change in Alpha-1 HDL Concentration Predicts Progression in Coronary Artery Stenosis. Arteriosclerosis Thromb Vasc Biol 23:847-852, May 2003.*
Seman L. et al. Lipoprotein(a) Cholesterol and Coronary Heart Disease in the Framingham Heart Study. Clinical Chemistry 45(7)1039-1046, Jul. 1999.*
Nozue T. et al. Effects of Statin on Small Dense Low Density Lipoprotein Cholesterol . . . J of Atherosclerosis and Thrombosis 15(3)146-153, 2008.*
Havekes et al., 1987, A rapid micro method for apolipoprotein E phenotyping directly in serum, J Lipid Res 28:455-63.
Heart Protection Study Collaborative Group, 2002, MRC/BHF Heart Protection Study of cholesterol lowering with simvastatin in 20,536 high-risk individuals: a randomised placebo-controlled trial, Lancet 360:7-22.
Hermann et al., 2006, Pharmacokinetics and Drug Disposition: Exposure of atorvastatin is unchangedbut lactone and acid metabolites are increased several-fold in patients with atorvastatin-induced myopathy, Clin Pharmacol Ther 79(6):532-539.

(Continued)

*Primary Examiner* — Ralph Gitomer
(74) *Attorney, Agent, or Firm* — Brown Rudnick LLP; Thomas C. Meyers (57) ABSTRACT

The invention provides methods for analyzing cardiovascular disease risk. Methods of the invention provide a probability of an individual developing cardiovascular disease based on parameters including blood levels of sdLDL-C, ApoA-I in α-1 HDL, and Lp(a) along with information about the patient's age and history of blood pressure treatment, smoking, and diabetes. Methods of the invention do not rely on standard risk factor measurements, such as CRP, total cholesterol, body mass index, weight, triglycerides, and the like.

5 Claims, 2 Drawing Sheets

(56) References Cited

U.S. PATENT DOCUMENTS

| | | |
|---|---|---|
| 2007/0218519 A1 | 9/2007 | Urdea et al. |
| 2008/0227210 A1 | 9/2008 | Smith |
| 2008/0269188 A1 | 10/2008 | Chapman et al. |
| 2008/0293054 A1 | 11/2008 | Medina et al. |
| 2008/0300170 A1 | 12/2008 | Gelber et al. |
| 2009/0197242 A1 | 8/2009 | Kaddurah-Daouk et al. |
| 2009/0246801 A1 | 10/2009 | Smith |
| 2009/0276161 A1* | 11/2009 | Cobain ............ G06F 19/3431 702/19 |
| 2010/0063153 A1 | 3/2010 | Chatterjee et al. |
| 2010/0076787 A1 | 3/2010 | Naylor et al. |
| 2010/0120136 A1 | 5/2010 | Larsen et al. |
| 2010/0167306 A1 | 7/2010 | Smith |
| 2010/0190172 A1 | 7/2010 | Cargill et al. |
| 2010/0204557 A1 | 8/2010 | Kiaie et al. |
| 2011/0112186 A1 | 5/2011 | Link et al. |
| 2011/0250618 A1 | 10/2011 | Nelson et al. |
| 2011/0269735 A1 | 11/2011 | Shiffman et al. |
| 2012/0065514 A1 | 3/2012 | Naghavi et al. |
| 2012/0288880 A1* | 11/2012 | Heinecke ............ G01N 33/92 435/7.92 |

FOREIGN PATENT DOCUMENTS

| | | |
|---|---|---|
| EP | 1 651 774 B1 | 9/2007 |
| WO | 02/48715 | 6/2002 |
| WO | 2004/050898 A2 | 6/2004 |
| WO | 2005/012566 A2 | 2/2005 |
| WO | 2006/008656 A2 | 1/2006 |
| WO | 2006/072654 A1 | 7/2006 |
| WO | 2007/061995 A2 | 5/2007 |
| WO | 2007/128884 A1 | 11/2007 |
| WO | 2008/131224 A2 | 10/2008 |
| WO | 2009/106838 A1 | 9/2009 |
| WO | 2011/058232 A1 | 5/2011 |
| WO | 2013/056087 A2 | 4/2013 |
| WO | 2013/078122 A1 | 5/2013 |
| WO | WO 2015/195662 | * 12/2015 |

OTHER PUBLICATIONS

Ho et al., 2006, Drug and bile acid transporters in rosuvastatin hepatic uptake: function, expression, and pharmacogenetics, Gastroent 130(6):1793-806.

Hsiang et al., 1999, A Novel Human Hepatic Organic Anion Transporting Polypeptide (OATP2), J Biol Chem 274(52):37161-37168.

International Hapman Consortium, 2005, A haplotype map of the human genome, Nature 437:1299-320.

International Search Report and Written Opinion mailed Apr. 5, 2013, for PCT/US12/60014 with International Filing Date Oct. 12, 2012 (9 pages).

International Search Report and Written Opinion mailed Feb. 18, 2015, for PCT/US2014/048022, with an International filing date of Jul. 24, 2014 (17 pages).

International Search Report and Written Opinion mailed Jan. 17, 2014, for International Application No. PCT/US2013/62241 with International filing date Sep. 27, 2013 (16 pages).

International Search Report and Written Opinion mailed Jan. 20, 2014, for PCT/US2013/066860 with International Filing Date Oct. 25, 2013 (14 pages).

International Search Report and Written Opinion mailed Mar. 3, 2016 for International Application No. PCT/US2015/061113 with International Filing Date Nov. 17, 2015 (10 Pages).

International Search Report mailed May 11, 2009, for PCT/GB2009/000547, with International Filing Date Feb. 27, 2009 (4 pages).

Isbell et al., 2007, Reproducibility and reliability of atherosclerotic plaque vol. measurements in peripheral arterial disease with cardiovascular magnetic resonance, J Cardiovasc Magn REson 9(1):71-76.

Jakulj et al., 2010, Baseline cholesterol absorption and the response to ezetimibe/simvastatin therapy: a post-hoc analysis of the ENHANCE trial, J Lipid Res 51:755-62.

Jones et al., 2003, Comparison of the efficacy and safety of rosuvastatin versus atorvastatin, simvastatin, and pravastatin across doses (STELLAR* Trial), Am J Cardiol 92:152-60.

Juraschek et al., 2012, Alternative markers of hyperglycemia and risk of diabetes, Diabetes Care 35(11):1-6.

Kajinami et al, 2004, CYP3A4 genotypes and plasma lipoprotein levels before and after treatment with atorvastatin in primary hypercholesterolemia, Am J Cardiol 93:104-7.

Kameyama et al., 2005, Functional characterization of SLC01B1 (OATP-C) variants, SLC01B1*5,SLC01B1*15 and SCL01B1*15+C1007G, by using transient expression systems of HeLa and HEK293 cells, Pharmacogenet Genomics 15(7): 513-522.

Kaput et al., 2007, Application of nutrigenomic concepts to Type 2 diabetes mellitus, Nutrition, Metabolism & Cardiovascular Diseases 17:89-103.

Kaput, 2004, Diet-disease gene interactions, Nutrition 20:26-31.

Kim et al., 2008, Increased systemic exposure to rosuvastatin in Asian subjects residing in the United States compared to Caucasian subjects, Clin Pharmacol Ther 83(supp 1):14.

Kim, 2004, 3-Hydroxy-3-methylglutaryl-coenzyme A reductase inhibitors (statins) and genetic variability(single nucleotide polymorphisms) in a hepatic drug uptake transporter: What's it all about?, Clin Pharmacol Ther 75(5):381-385.

Kivistö and Niemi, 2006, Influence of Drug Transporter Polymorphisms on Pravastatin Pharmacokinetics in Humans, Pharmaceut Res 24(2):239-247.

Kolberg et al., 2009, Development of a Type 2 Diabetes Risk Model From a Panel of Serum Biomarkers From the Inter99 Cohort, Diabetes Care 32(7):1207-1212.

Konig et al., 2006, Pharmacogenomics of human OATP transporters, Naunyn Schmiedeberg's Arch Pharmacol 372:432-43.

Krakoff et al., 2003, Inflammatory Markers, Adiponectin, and Risk of Type 2 Diabetes in the Pima Indian, Diabetes Care 26(6):1745-1751.

Lakoski et al., 2010, Indices of Cholesterol Metabolism and Relative Responsiveness to Ezetimibe and Simvastatin, J Clin Endocrinol Metab 95(2):800-809.

Lamon-Fava et al., 2007, Effects of different doses of atorvastatin on human apolipoprotein B-100, B-48, and A-I metabolism, J Lipid Res 48:1746-53.

Law et al., 2006, Statin safety: a systematic review, Am J. Cardiol, 97(8A):52C-60C.

Lindstrom, 2003, The Diabetes Risk Score, Diabetes Care 26(3):725-731.

Link et al., 2008, SLC01B1 variants and statin-induced myopathy-a genomewide study, NEJM 359(8):789-799.

Lund et al., 1989, Determination of serum levels of unesterified lathosterol by isotope dilution-mass spectrometry, Scand J Clin Lab Inv 49:165-171.

Luzón-Toro et al., 2007, Gas chromatographic-mass spectrometric determination of brain levels of ?-cholest-8-en-3?-ol(lathosterol), J Chromatogr B 850:177-182.

Lyssenko et al., 2005, Genetic Prediction of Future Type 2 Diabetes, PLoS Medicine 2(12):e345.

Madsbad et al., 2004, Improved Glycemic Control With no. Weight Increase in Patients With Type 2 Diabetes After Once-Daily Treatment With the Long-Acting Glucagon-Like Peptide 1 Analog Liraglutide (NN2211), Diabetes Care 27(6):1335-1342.

Mangravite et al., 2006, Clinical implications of pharmacogenomics of statin treatment, Pharmacogenomics J, 6:360-374.

Mann et al., 2010, Comparative Validity of 3 Diabetes Mellitus Risk Prediction Scoring Models in a Multiethnic US Cohort, Am J Epidemiol 171(9):980-988.

Matthan et al., 2000, Deuterium uptake and plasma cholesterol precursor levels correspond as methods for measurement of endogenous cholesterol synthesis in hypercholesterolemic women, Lipids 35(9):1037-1044.

Matthan et al., 2003, Impact of simvastatin, niacin, and/or antioxidants on cholesterol metabolism in CAD patients with low HDL, J Lipid Res. 44:800-806.

(56) References Cited

OTHER PUBLICATIONS

Matthan et al., 2009, Cholesterol absorption and synthesis markers in individuals with and without a CHD event during pravastatin therapy: insights from the PROSPER trial, J Lipid Res 51:202-209.
Miettinen et al., 1990, Serum plant sterols and cholesterol precursors reflect cholesterol absorption and synthesis in volunteers of a randomly selected male population. Am J Epidemiol 131(1):20-31.
Miettinen et al., 2000, Noncholesterol sterols and cholesterol lowering by long-term simvastatin treatment in coronary patients: relation to basal serum cholestanol, Arterioscler Thromb Vasc Biol 20:1340-1346.
Miettinen et al., 2000, Noncholesterol Sterols and Cholesterol Lowering by Long-Term Simvastatin Treatment in Coronary Patients: Relation to Basal Serum Cholestanol, Arteriosclerosis, Thrombosis, and Vascular Biology 20(3):1340-1346.
Miettinen et al., 2003, Serum noncholesterol sterols during inhibition of cholesterol synthesis by statins, J Lab Clin Med 141:131-137.
Molden, 2004, Variability in cytochrome P450-mediated metabolism of cardiovascular drugs: clinical implications and practical attempts to avoid potential problems, Heart Drug 4:55-79.
Morimoto et al, 2004, A novel variant allele of OATP-C (SLCO1B1) found in a Japan patient with pravastatin-induced myopathy, Drug Metab Pharmocokinet 19:453-455.
Morimoto et al., 2003, Candidate gene approach for the study of genetic factors involved in HMG-CoA reductase inhibitor-induced rhabdomyolysis, Eighteenth JSSX Annual Meeting 8PE-32.
Morimoto et al., 2005, OATP-C(OATP01B1)*15 is associated with statin-induced myopathy in hypercholesterolemia patients, Clin Pharmacol Ther 77(2):P21.
Morrone et al., 2012, Lipid-altering efficacy of ezetimibe plus statin and statin monotherapy and identification of factors associated with treatment response: A pooled analysis of over 21,000 subjects from 27 clinical trials, Atherosclerosis 223:251-261.
Mulder et al., 2001, Association of polymorphism in the cytochrome CYP2D6 and the efficacy and tolerability of simvastatin, Clin Pharmacol Ther 70(6):546-551.
Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.
van Himbergen et al., 2009, Comparison of the effects of maximal dose atorvastatin and rosuvastatin therapy on cholesterol synthesis and absorption markers, J Lipid Res 50:730-739.
Vanhanen and Miettinen, 1992, Pravastatin and lovastatin similarly reduce serum cholesterol and its precursor levels in familial hypercholesterolaemia, Eur J Clin Pharmacol 42:127-130.
Vladutiu et al., 2006, Genetic risk factors associated with lipid-lowering drug-induced myopathies, Muscle Nerve 34:153-162.
Voors et al., 2009, The SLCO1B18*5 Genetic Variant is Associated with Statin-Induced Side Effects, J Am Coll Cardiol 54(17):1609-1616.
Warnick et al., 2001, Evolution of methods for measurement of HDL-Cholesterol: From ultracentrifugation to homogeneous assays, Clin Chem 47(9):1579-1596.
Wellcome Trust Case Control Consortium, 2007, Genome-wide association study of 14,000 cases of seven common diseases and 3,000 shared controls, Nature 447(7):661-678.
Weng et al., 2010, A systematic review and meta-analysis on the therapeutic equivalence of statins, J Clin Pharm Ther 35:139-151.
Wilson et al., 2007, Prediction of Incident Diabetes Mellitus in Middle-aged Adults, Arch Intern Med 167:1068-1074.
Wilson et al., 2007, The Framingham offspring study, prediction of incident diabetes mellitus in middle-aged adults, Arch Intern Med 167(10):1068-1074.
Xu et al., 2007, Organic anion transporting polypeptide-1B1 haplotypes in Chinese patients, Acta Pharmacologica Sinica, 28(10):1693-1697.
Zocor datasheet, 2007.httD://www.emc.medicines.ora.uk/emc/assets/c/htmllDisDlavDoc.asD?DocumentID=120.
Zuccaro et al., 2007, Tolerability of statins is not linked to CYP450 polymorphisms, but reduced CYP2D6 metabolism improves cholesteraemic response to simvastatin and fluvastatin, Pharmacol Res 55:310-317.
Márk et al., 2007, Change in the cholesterol metabolism associated with the combined inhibition of synthesis and absorption, Orvosi Hetilap 148:14:627-632.
Nauck et al., 2002, Methods for measurement of LDL-Cholesterol: a critical assessment of direct measurement by homogeneous assays versus calculation, Clin Chem 48(2):236-254.
Niemi et al., 2004, High plasma pravastatin concentrations are associated with single nucleotide polymorphisms and haplotypes of organic anion transporting polypeptide-C (OATP-C, SCL01B1), Pharmacogenetics 14:429-440.
Niemi et al., 2005, Acute effects of pravastatin on cholesterol synthesis are associated with SLC01B1(encoding OATP1B1) haplotype *17, Pharmacogenet. Genomics 15(5):303-309.
Niemi et al., 2011, Organic anion transporting polypeptide 1B1: a genetically polymorphic transporter of major impotance for hepatic drug uptake, Pharmacol Rev 63(1):157-181.
Nishizato et al., 2003, Polymorphisms of OATP-C (SLC21A6) and OAT3 (SLC22A8) genes: Consequences for pravastatin pharmacokinetics, Clin Pharmacol Ther 73(6):554-565.
Nissinen et al., 2010, Applicability of non-cholesterol sterols in predicting response in cholesterol metabolism to simvastatin and fluvastatin treatment among hypercholesterolemic men, Nutr Metab Cardiovasc Dis 20:308-316.
Nozawa et al., 2002, Genetic polymorphisms of human organic anion transporters OATP-C(SLC21A6) and OATP-B (SLC21A9): Allele frequiences in the Japanese population and functional analysis, J Pharmacol Exp Ther 302(2):804-813.
Oh et al., 2007, Genetic determinants of statin intolerance, Lipids Health Dis, 6:7.
Ooi et. al., 2008, Dose-dependent effect of rosuvastatin on apolipoprotein B-100 kinetics in the metabolic syndrome, Atherosclerosis 197:139-46.
Ordovas JM et al, The APOE Locus and the Pharmacogenetics of Lipid Response, Cur Opin Lipidol 13:113-117, 2002.
Pasanen et al., 2006, Frequencies of single nucleotide polymorphisms and haplotypes of organic anion transporting polypeptide 1B1 SLCO1B1 gene in a Finnish population, Eur J Clin Pharmacol 62:409-415.
Pasanen et al., 2006, SLC01B1 polymorphism markedly affects the pharmacokinetics of simvastatinacid, Pharmacogenet Genomics 16(12):873-879.
Pasanen et al., 2007, Different effects of SLC01B1 polymorphism on the pharmacokinetics of Atorvastatin and Rosuvastatin, Clin Pharmacol Ther 82(6):726-733.
Pasanen et al., 2008, Global analysis of genetic variation in SLC01B1, Pharmacogenomics 9(1):19-33.
Patent Examination Report No. 1 date of issue Jun. 11, 2014 for Patent Application No. AU 20111261480.
Pearson et al., 2005, A community-based, randomized trial of ezetimibe added to statin therapy to attain NCEP ATP III goals for LDL cholesterol in hypercholesterolemic patients: the ezetimibe add-on to statin for effectiveness (EASE) trial, Mayo Clin Proc 80:587-595.
Pearson et al., 2006, Effectiveness of ezetimibe added to ongoing statin therapy in modifying lipid profiles and low-density lipoprotein cholesterol goal attainment in patients of different races and ethnicities: a substudy of the Ezetimibe add-on to statin for effectiveness trial, Mayo Clin Proc 81:1177-1185.
Perk et al., 2012, European guidelines on cardiovascular disease prevention in clinical practice (version 2012): The Fifth Joint Task Force of the European Society of Cardiology and Other Societies on Cardiovascular Disease Prevention in Clinical Practice Cardiovascular Prevention & Rehabilitation, Eur Heart J 33:1635-1701.
Posch et al., 2007, A Language and Environment for Statistical Computing, Vienna, Austria: R Foundation for Statistical Computing.
Pradhan et al., 2001, C-Reactive Protein, Interleukin 6, and Risk of Developing Type 2 Diabetes Mellitus, JAMA 286(3)327-334.

(56) References Cited

OTHER PUBLICATIONS

Price et al., 2006, Principle components analysis corrects for stratification in genome-wide association studies, Nat Genet 38(8):904-909.
Purcell et al., 2007, PLINK: a tool set for whole-genome association and population-based linkage analyses, Am J Hum Genet 81:559-575.
Ravussin, 2002, Adiponectin enhances insulin action by decreasing ectopic fat deposition, The Pharmacogenomics Journal 2:4-7.
Reihnér et al., 1990, Influence of pravastatin, a specific inhibitor of HMG-CoA reductase, on hepatic metabolism of cholesterol, NEJM 323(4):224-228.
Robinson, 2007, Simvastatin: present and future perspectives, Expert Opin. Pharmacother. 8(13):2159-2172.
Romaine SPR et al, The Influence of SLC01B1 (OATP1B1) Gene Polymorphisms on Response to Statin Therapy, Pharmacogenom J 10:1-11, 2010.
Ruano et al., 2007, Physiogenomic association of statin-related myalgia to serotonin receptors, Muscle Nerve 36:329-335.
Schaefer et al., 2012, Association of statin potency with markers of cholesterol absorption/synthesis and LDL-C lowering efficacy of ezetimibe add on therapy, J of Clinical Lipidology 6(3):286.
Schaffer et al., 1982, Comparison of two isotope dilution/mass spectrometric methods for determination of total serum cholesterol, Clin Chem 28(1):5-8.
Schmidt et al., 2005, The atherosclerosis risk in communities study, Diabetes Care 28(8):2013-2018.
Search Study Collaborative Group, 2007, Study of the effectiveness of additional reductions in cholesterol and homocysteine (SEARCH): characteristics of a randomized trial among 12064 myocardial infarction survivors, Am Heart J 154(5):815-823.
Search Study Collaborative Group, 2008, SLC01B1 variants and statin-induced myopathy—a genomewide study, NEJM 359(8):789-799.
Shitara et al., 2006, Pharmacokinetic and pharmacodynamic alterations of 3-hydroxy- 3-methylglutaryl coenzyme A (HMG-CoA) reductase inhibitors: drug-drug interactions and interindividual differences in transporter and metabolic enzyme functions, Pharmacol Ther 112:71-105.
Simonson et al., 2004, Rosuvastatin pharmacokinetics in heart transplant recipients administered an antirejection regimen including cyclosporine, Clin Pharmacol Ther 76:167-77.
Spranger et al., 2003, Adiponectin and protection against type 2 diabetes mellitus, Lancet 361:226-228.
Stern et al., 1984, The San Antonio Heart Study, sex difference in the effects of sociocultural status on diabetes and cardiovascular risk factors in Mexican Americans, Am J Epidemiol 120(6):834-851.
Stern et al., 1993, Predicting diabetes, moving beyond impaired glucose tolerance, Diabetes 42:706-714.
Streiner et al., 2011, Correction for multiple testing, is there a resolution?, Chest, 140(1):16-18.
Sturis et al., 2003, GLP-1 derivative liraglutide in rats with b-cell deficiencies: influence of metabolic state on b-cell mass dynamics, British Journal of Pharmacology 140:123-132.
Sudhop et al., 2002, Inhibition of intestinal cholesterol absorption by ezetimibe in humans, Circulation 106:1943-1948.
Sugiuchi et al., 1998, Homogeneous assay for measuring low-density lipoprotein cholesterol in serum with triblock copolymer and a-cyclodextrin sulfate, Clin Chem 44(3):522-531.
Third Report of the National Cholesterol Education Program (NCEP) Expert Panel on Detection, Evaluation, and Treatment of High Blood Cholesterol in Adults (Adult Treatment Panel III) final report. Circulation 2002,106:3143-3421.
Thompson et al., 2002, Why some patients respond poorly to statins and how this might be remedied, European Heart Journal 23(3):200-206.
Thompson et al., 2003, Statin-associated myopathy, JAMA 289:1681-1690.
Thongtang et al, 2012, Effects of ezetimibe added to statin therapy on markers of cholesterol absorption and synthesis and LCL-C lowering in hyperlipidemic patients, Atherosclerosis 225(2):388:396.
Tirona et al., 2001, Polymorphisms in OATP-C: identification of multiple allelic variants associated with altered transport activity among European- and African-Americans, J Biol Chem 276:35669-35675.
Tobert, 2003, Lovastatin and beyond: The history of the HMG-CoA reductase inhibitors, Nat Rev Drug Discov 2(7):517-526.
Tyburczy et al., 2012, Evaluation of low trans-fat edible oils by attenuated total reflection-Fourier transform infrared spectroscopy and gas chromatography: a comparison of analytical approaches, Anal Bioanal Chem 404(3):809-819.
United Kingdom Search Report issued in application No. GB0803833.3 on Jun. 27, 2008.
Ahem et al., 1995, Biochemical, Reagent Kits Offer Scientists Good Return on Investment, The Science 9:1-5.
Akao et al., 2012, Genetic Variation at the SLC01B1 Gene Locus and Low Density Lipoprotein Cholesterol Lowering Response to Pravastatin in the Elderly, Atherosclerosis 220:413-417.
Anderson, 2010, The Clinical Plasma Proteome: A Survey of Clinical Assays for Proteins in Plasma and Serum, Clinical Chemistry 56(2):177-185.
Armitage, 2007, The safety of statins in clinical practice, Lancet 370:1781-90.
Assmann et al., 2008, Effects of ezetimibe, simvastatin, atorvastatin, and ezetimibe-statin therapies on non-cholesterol sterols in patients with primary hypercholesterolemia, Curr Med Res Opin 24:249-59.
Asztalos et al., 2004, High-density Lipoprotein Subpopulation Profile and Coronary Heart Disease Prevalence in Male Participants of the Framingham Offspring Study, Arterioscler Thromb Vasc Biol 24(11):2181-7.
Asztalos et al., 2005, Value of High-Density Lipoprotein (HDL) Subpopulations in Predicting Recurrent Cardiovascular Events in the Veterans Affairs HDL Intervention Trial, Arterioscler Thromb Vasc Bio 25(10):2185-2191.
Asztalos et al., 2006, LpA-I, LpA-I:A-II HDL and CHD-risk: The Framingham Offspring Study and the Veterans Affairs HDL Intervention Trial, Atherosclerosis 188(1)59-67.
Asztalos, 1993, Two-dimensional electrophoresis of plasma lipoproteins: recognition of new apo A-I-containing subpopulations, Biochim Biophys Acta 1169(3):291-300.
Asztalos, 2000, Distribution of ApoA-I-containing HDL Subpopulations in Patients with Coronary Heart Disease, Arterioscler Thromb Vasc Biol 20(12)2670-6.
Ballantyne et al. Effect of ezetimibe coadministered with atorvastatin in 628 patients with primary hypercholesterolemia: a prospective, randomized, double-blind trial. Circulation 2003;107:2409-15.
Ballantyne et al., 2003, Risk for myopathy with statin therapy in high-risk patients, Arch Intern Med 163:553-64.
Barrett et al., 2005, Haploview: analysis and visualization of LD and haplotype maps, Bioinformatics 21:263-5.
Bland et al., 1995, Multiple significance tests: the Bonferroni method, BMJ 310:170.
Brambilla et al., 2011, Normal Fasting Plasma Glucose and Risk of Type 2 Diabetes, Diabetes Care 34:1372-1374.
Burke et al., 1974, Mechanisms of the Liebermann-Burchard and Zak Color Reactions for Cholesterol, Clin Chem 20(7):794-801.
Burke, J. P., et al., "Rapid Rise in the Incidence of Type 2 Diabetes From 1987 to 1996," (1999) Arch Intern Med. 159:1450-1456.
Camont et al., 2011, Biological activities of HDL subpopulations and their relevance to cardiovascular disease, Trends Mol Med 17(10):594-603.
Carlton et al., 2006, Functional single nucleotide polymorphism-based association studies, Human Genomics 2(6):391-402.
Catapano et al., 2011, ESC/EAS Guidelines for the management of dyslipidaemias the Task Force for the management of dyslipidaemias of the European Society of Cardiology (ESC) and the European Atherosclerosis Society (EAS), Atherosclerosis 217:3-46.

(56) References Cited

OTHER PUBLICATIONS

Corsini et al., 2005, Pharmacokinetic interactions between statins and fibrates, Am J Cardiol 96:44K-49K.
Couvert et al., 2008, Association between a Frequent Allele of the Gene Encoding OATP1B1 and the Enhanced LDL-Lowering Response to Fluvastatin Therapy, Pharmacogenomics 9:1217-1227.
Cruz et al., 2004, Low Adiponectin Levels Predict Type 2 Diabetes in Mexican Children, Diabetes Care 27(6):1451-1453.
CTT, 2005, Efficacy and safety of cholesterol-lowering treatment: prospective meta-analysis of data from 90056 participants in 14randomised trials of statins, Lancet 366:1267-78.
Davidson et al., 2002, Ezetimibe coadministered with simvastatin in patients with primary hypercholesterolemia, J Am Coll Cardiol 40:2125-34.
Davidson et al., 2004, Efficacy and safety of ezetimibe coadministered with statins: randomised, placebo-controlled, blinded experience in 2382 patients with primary hypercholesterolemia, Int J Clin Pract 58:746-55.
Davis, H et al. Zetia: Inhibition of Niemann-Pick C1 Like 1 (NPC1L1) to Reduce Intestinal Cholesterol Absorption and Treat Hyperlipidemia. Journal of Atherosclerosis and Thrombosis. May 2007, vol. 14; pp. 99-108.
De Cuyper et al., 1993, Determination of changes in serum lathosterol during treatment with simvastatin to evaluate the role of lathosterol as a parameter for whole body cholesterol synthesis, Clin Chim Acta 219:123-30.
Degn et al., 2004, One Week's Treatment With the Long-Acting Glucagon-Like Peptide 1 Derivative Liraglutide (NN2211) Markedly Improves 24-h Glycemia and-and-Cell Function and Reduces Endogenous Glucose Release in Patients with Type 2 Diabetes, Diabetes 53:1187-1194.
Devlin et al., 1999, Genomic control for association studies, Biometrics 55:997-1004.
Dullaart et al., 1996, The serum lathosterol to cholesterol ratio, an index of cholesterol synthesis, is not elevated in patients with glomerular proteinuria and is not associated with improvement of hyperlipidemia in response to antiproteinuric treatment, Metabolism 45(6):723-730.
Eddy et al., 2003, A trial-validated model of diabetes, Diabetes Care 26(11):3093-3101.
Eddy et al., 2003, Validation of the Archimedes Diabetes Model, Diabetes Care 26(11):3102-3110.
Espy et al., 2006, Real-time PCR in clinical microbiology: applications for routine laboratory testing, Clin Microbiol Rev 19(1):165-256.
Etu-Seppala et al., 2003, Programme for the Prevention of Type 2 Diabetes in Finland, Finnish Diabetes Association 2003-2010.
Farnier, M et al. Lipid-Altering Eficacy of Ezetimibe/Simvastatin 10/20 mg Compared With Rosuvastatin 10 mg in High-Risk Hypercholesterolaemic Patients Inadequately Controlled With Prior Statin Monotherapy—The IN-CROSS Study. The International Journal of Clinical Practice. Apr. 2009, vol. 63; pp. 547-559.
Fiegenbaum et al., "The role of common variants of ABCB1, CYP3A4, and CYP3A5 genes in lipidlowering efficacy and safety of simvastatin treatment," Clin. Pharmocol. Ther., vol. 78, pp. 551-558, 2005.
Friedewald et al., 1972, Estimation of the concentration of low-density lipoprotein cholesterol in plasma, without use of the preparative ultracentrifuge, Clin Chem 18:499-502.
Frudakis et al., 2007, CYP2D6*4 polymorphism is associated with statin-induced muscle effects,Pharmacogenetics and Genomics, 17:695-707.
Fumeron et al., 2004, Adiponectin Gene Polymorphisms and Adiponectin Levels Are Independently Associated With the Development of Hyperglycemia During a 3-Year Period; The Epidemiologic Data on the Insulin Resistance Syndrome Prospective Study, Diabetes 53:1150-1157.
Gagne et al., 2002, Efficacy and safety of ezetimibe coadministered with atorvastatin or simvastatin in patients with homozygous familial hypercholesterolemia, Circulation 105:2469-75.
Gazi et al., 2007, Effect of ezetimibe in patients who cannot tolerate statins or cannot get to the low density lipoprotein cholesterol target despite taking a statin, Curr Med Res Opin 23(9):2183-2192.
Generaux GT et al, Impact of SLCOI B1 (OATP1 B1) and ABCG2 (BCRP) Genetic Polymorphisms and Inhibition on LDL-C Lowering and Myopathy of Statins, Xenobiot 41 : 639-651, 2011.
Goh et al., 1989, HPLC analysis of desmosterol, 7-dehydrocholesterol, and cholesterol, Lipids 24.7:652-655.
Gordon et al., 1989, High-density Lipoprotein Cholesterol and Cardiovascular Disease. Four Prospective American Studies, Circulation 79(1):8-15.
Gouni et al. Effects of ezetimibe and/or simvastatin on LDL receptor protein expression and on LDL receptor and HMG-CoA reductase gene expression: a randomized trial in healthy men. Atherosclerosis 2008;198:198-207.
Grundy et al., 2004, Implications of recent clinical trials for the National Cholesterol Education Program Adult Treatment Panel III guidelines, Circulation 110:227-39.
Grundy et al., 2013, Plasma Non-Cholesterol Sterols as Indicators of Cholesterol Absorption, J Lipid Res 54:873-875.
Gunderson et al., 2006, Whole-genome genotyping of haplotype tag single nucleotide polymorphisms, Pharmacogenomics 7:641-8.
Harder et al., 2004, The Effect of Liraglutide, a Long-Acting Glucagon-Like Peptide 1 Derivative, on Glycemic Control, Body Composition, and 24-h Energy Expenditure in Patients; With Type 2 Diabetes, Diabetes Care 27(8):1915-1921.

\* cited by examiner

CARDIOVASCULAR DISEASE RISK ASSESSMENT

RELATED APPLICATIONS

This Application claims priority to U.S. Provisional Application No. 62/080,833, filed Nov. 17, 2014, which is incorporated by reference in its entirety.

FIELD OF THE INVENTION

The present invention generally relates to predicting cardiovascular risk.

BACKGROUND

Cardiovascular disease (CVD), consisting of coronary heart disease (CHD), stroke, carotid artery disease, and peripheral vascular disease (PVD), is the leading cause of death in the United States. About 82.6 million Americans have some form of CVD (39% of the population). Average US life expectancy is 77.9 years. Age-adjusted CVD death rates decreased 32.8% between 1998 and 2008. 1 in 3 of all deaths (2.471 million) are from CVD, and about 1 in 2 known causes of death. In 2009 there are 150,000 CVD deaths in people <65 yrs.

Every 25 seconds someone in the United States has a heart attack (2,718/day), and every 40 seconds someone has a stroke (2,178/day). Of the 2.437 million deaths in the United States in 2009 according to the National Center for Health Statistics 24.6% are from CHD, 5.3% are from stroke, and another 4.7% are from diabetes and kidney disease (most deaths are due to CVD). In 2008 there are 785,000 new CHD events/year, 470,000 recurrent CHD events, and 195,000 silent heart attacks. According to the CDC 15.26 million people (6%) have CHD, 59.26 million (25%) have high blood pressure, and 6.23 million (3%) have had a stroke.

Many of the more serious complications of CVD can be treated or prevented through early detection and identification of at risk individuals. Early treatment and lifestyle adjustments are key to preventing CVD progression and complications. Current methods of identifying populations with elevated risk of CVD are not accurate enough to encourage patients to make difficult lifestyle changes or to support recommendations for treatments that may carry a risk of negative side effects.

SUMMARY

The invention provides improved methods for analyzing cardiovascular disease risk. According to the invention, an algorithm that considers LDL and HDL subfractions, along with lipoprotein a (Lp(a)) provides significant improvement in predicting CVD versus standard assays that include standard risk factors. Methods of the invention comprise measuring LDL and HDL subfractions in addition to Lp(a) without reference to standard risk factor measurements, such as CRP, total cholesterol, body mass index, weight, triglycerides, and the like. It is unexpected that an algorithm focusing only on LDL and HDL subfractions and Lp(a) would be more informative as to CVD risk than measurements that are much more comprehensive in terms of the markers that are reviewed. In particular, the sdLDL-C subfraction of LDL and the ApoA-1 in large alpha-1 HDL are most informative in conjunction with Lp(a).

In certain aspects, the invention provides a method for assessing cardiovascular risk. The method includes conducting an assay to determine blood levels of an LDL subfraction, an HDL subfraction, and Lp(a) as well as subjecting the levels to an algorithm to determine whether one or more of the LDL subfraction, the HDL subfraction, and the Lp(a) are statistically different than predetermined thresholds. Further, the method includes assessing cardiovascular risk based upon results of the algorithm. Preferably, neither the conducting step nor the subjecting step considers C-Reactive protein.

In some embodiments, the method includes obtaining information about one or more of a patient's age, history of blood pressure treatment, smoking, and diabetes; and including the information in the subjecting step. The conducting step and the subjecting step can each ignore any measure of triglycerides, total cholesterol, body mass index, waist circumference, and use of cholesterol or glucose lowering medication. Any suitable assay may be used such as, for example, an enzymatic assay, high-performance liquid chromatography, affinity chromatography, an immunoassay, a radioassay, an enzyme-linked immunosorbent assay, colorimetry, and an electrochemical assay. The assay may be performed on a sample obtained from a patient. In some embodiments, a therapy (e.g., a statin) is administered to the patient based on the assessed cardiovascular risk. The method may be used to produce a report describing the cardiovascular risk for the patient. For example, the report may be provided to the patient printed on paper.

Aspects of the invention provide a method of predicting the risk of a patient developing cardiovascular disease. The method includes the steps of obtaining a sample from the patient who presents as negative for cardiovascular disease; conducting an assay on the sample to determine a level of small, dense low-density lipoprotein cholesterol (sdLDL-C) in the sample; conducting an assay on the sample to determine a level of lipoprotein(a) (Lp(a)) in the sample; conducting an assay on the sample to determine a level of apolipoprotein A-I (apoA-I) in the sample; and entering said levels into a multivariate model to predict a risk of the patient developing cardiovascular disease. Preferably, the level of apoA-I in the sample comprises the level of apoA-I in large α-high-density lipoprotein cholesterol in the sample.

In certain aspects, the invention provides a method for assessing cardiovascular risk. The method includes obtaining a sample from a patient and conducting an assay on the sample to determine blood levels of an LDL subfraction, an HDL subfraction, and Lp(a). The levels are entered into a multivariate model to produce a probability of the individual developing cardiovascular disease. In certain embodiments, methods may include obtaining information about one or more of the patient's age, history of blood pressure treatment, smoking, and diabetes and entering the obtained information into the multivariate model. In various embodiments, the multivariate model does not include a C-Reactive protein level and in some embodiments, the model does not include triglycerides, total cholesterol, body mass index, waist circumference, patient use of cholesterol lowering medication, and patient use of glucose lowering medication.

Methods of the invention may include an assay such as an enzymatic assay, high-performance liquid chromatography, affinity chromatography, an immunoassay, a radioassay, an enzyme-linked immunosorbent assay, colorimetry, or an electrochemical assay. Methods may include administering a therapy to the patient based on the assessed cardiovascular risk. The therapy may include administering a statin drug or ezetimibe or recommending or implementing lifestyle changes. In certain embodiments methods include producing a report describing the In certain aspects, the invention provides a system for analyzing cardiovascular disease (CVD) hazards. The system includes a processor coupled to a memory subsystem having instructions stored therein that when executed by the processor cause the system to perform a number of steps. These steps include creating a record for a subject and obtaining for the subject and storing in the record a set of subject levels that include an SdLDL-C level (mg/dL), a level of ApoA-1 in a-1 HDL (mg/dL), and a Lipoprotein(a) level (mg/dL). Steps executed by the system also include appending, to the record, information for the subject for age (years), smoker status (y/n), use of blood pressure medication (y/n). Additional steps include retrieving a pre-determined coefficient set from the memory subsystem; applying the predetermined coefficient set to the set of subject levels to determine an a CVD hazard factor (x); and operating an output device operably connected to the processor to provide a report indicating a level of future CVD hazard for the subject.

In certain embodiments, the processor may operate to send the report from the output device to a medical facility. The predetermined coefficient set may consist of numerical coefficients A, B, C, D, E, F, and G, wherein the CVD hazard factor (x) is determined according to the following: x=A+ B*(the age)+C*(the smoker status)+D*(the SdLDL-C level)+E*(the level of ApoA-1 in a-1 HDL)+F*(log(Lipoprotein(a)) level)+G*(the use of blood pressure medication).

In certain embodiments, the memory subsystem may have instructions stored therein that when executed by the processor, cause the system to further determine from the CVD hazard factor, a probability (p) of the subject developing CVD wherein $p=1/(1+e^{(-x)})$. In various embodiments, A may be within 25% of −6.4752, B may be within 25% of +0.0655, C may be within 25% of +0.5816, D may be within 25% of +0.0144, E may be within 25% of −0.0235, F may be within 25% of +0.257, and G may be within 25% of +0.6254. In certain embodiments, A may be −6.4752, B may be +0.0655, C may be +0.5816, D may be +0.0144, E may be −0.0235, F may be +0.257, and G may be +0.6254.

The report may indicates a high risk of CVD for the subject when p >0.5 and the output device may include a network interface card (nic) and the report may comprise a file provided to the medical facility using the nic.

DETAILED DESCRIPTION

The invention provides assays and improved methods for analyzing cardiovascular disease risk. The invention relates to algorithms for determining elevated risk of developing CVD with increased accuracy over current recommended standards such as those promulgated in Goff Jr D C, et al., 2013 ACC/AHA Guideline on the Assessment of Cardiovascular Risk, Journal of the American College of Cardiology(2013), doi: 10.1016/j.jacc.2013.11.005. According to the invention, an algorithm considering LDL and HDL subfractions (e.g., small, dense LDL-C and apolipoprotein A-I (apoA-I) level in large α-1 HDL-C) along with Lp(a) may be used to indicate an elevated risk of developing CVD. Algorithms of the invention may also account for patient age and/or gender along with a patient's history of smoking, diabetes, and/or blood pressure treatment.

Figure 1:
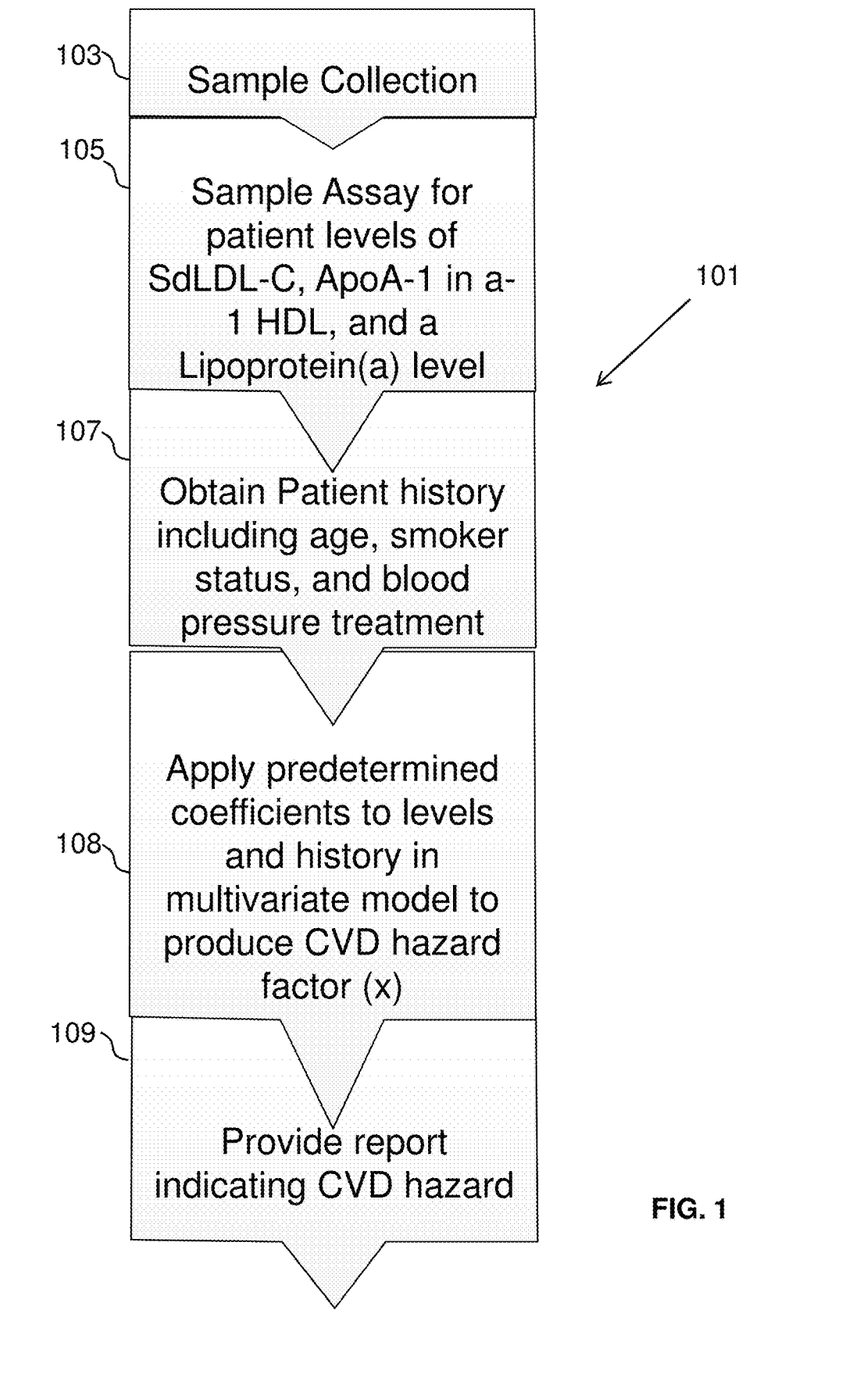
FIG. 1 diagrams an exemplary method of the invention.

FIG. 1 diagrams an exemplary method 101 of the invention. In the diagramed method 101, a sample may be collected from a subject 103 and one or more assays performed on the sample to determine subject levels of SdLDL-C, ApoA-1 in a-1 HDL, and a Lipoprotein(a) 105. Patient information may be obtained related to the patient's age, smoking status, and blood pressure treatment or medication 107. Predetermined coefficients may then be applied to the levels and history in multivariate model to produce CVD hazard factor (x) 108. Once a CVD hazard factor is determined, it may be provided in a report 109.

Methods may include measuring the concentration of apo A-I (the major protein of HDL) in individual HDL particles after they have been separated by two dimensional gel electrophoresis and imaged with an apoA-I specific antibody. Other approaches include separating HDL by ultracentrifugation and then stain the protein or measure the cholesterol, or measure nuclear magnetic resonance (NMR) fatty acid signals to obtain estimations of HDL particles. Other approaches include separating HDL particles by ion mobility.

There are five major apoA-I containing HDL particles, with various functions. Very small preβ-1 HDL pick up cholesterol from cells, and are coverted to small α-4 HDL. The cholesterol on α-4 HDL particles has a fatty acid attached to it to become cholesteryl ester in the core of HDL, and the α-4 HDL are converted to medium α-3 HDL, large α-2 HDL, and finally to very large α-1 HDL. Cholesteryl ester on the medium α-3 HDL can also be transferred to triglyceride-rich lipoproteins. Alternatively α-3 HDL can enlarge to large α-2 and very large α-1 HDL than donates cholesterol to the liver for removal from the body. The apoA-I can recycle back to very small HDL particles.

Low levels of apoA-I in the very large α-1 HDL have been shown to be a much better predictors of CHD than HDL-C or apoA-I levels alone (40-42). Based on studies in participants in the Framing Offspring Study, for every 1 mg/dL increase in apoA-I in the very large α-1 HDL particles there was a 26% decrease in CVD risk. Optimizing the levels of these particles is linked with the statin/niacin combination to significant regression of coronary artery atherosclerosis. Both significant weight loss, niacin alone and statin alone can have very beneficial effects on normalizing HDL particles (lowering very small pre-β-1 HDL and raising very large α-1 HDL). In CVD patients already on statin therapy those with elevated triglycerides (>200 mg/dL) and low HDL cholesterol (<35 mg/dL) get substantial CVD risk reduction when niacin is added to statin therapy (14). The same is true for diabetics already on statin therapy in terms of getting benefit from the addition of fenofibrate treatment (19). Our measurement of HDL particles can precisely identify which patients require and will benefit from niacin or fenofibrate when they are already receiving statin treatment.

The term "α-1 HDL particle" or "α-1", as used herein, refers to the apoA-I concentration in the HDL particles with a median size of about 11.0 nm. It is one of the most important HDL particles for predicting heart disease. This large particle delivers cholesterol to the liver. This HDL particle is large and lipid-rich; it contains 6 molecules of apoA-I, a large amount of free cholesterol and phospholipids (PL) on the surface, and cholesterol ester and TG in the core. This is the particle that interacts with scavenger receptor B1 (SRB1) in the liver and dumps cholesterol into the bile. A decreased level marks an inadequate HDL metabolism and is associated with increased risk for CVD. A value below 12.0 mg/dl is associated with increased heart disease risk in men and a value below 18.0 mg/dl is associated with increased heart disease risk in women, while a value between 12.0 mg/dl and 17.0 mg/dl in men and a value between 18.0 mg/dl and 28.0 mg/dl in women is considered borderline. A value above 17.0 mg/dl in men and above 28.0 mg/dl in women is considered normal.

The term "apolipoprotein A-I" or "apoA-I", as used herein, refers to the measure of the most abundant protein component of HDL having a 28 kilo Daltons (KD) molecular weight. ApoA-I is an essential component of HDL; low level of apoA-I is associated with low level of HDL-C and high risk for CVD.

HDL subpopulation analysis by two-dimensional gel electrophoresis involves separation of lipoproteins. HDL can be separated by electrophoretic mobility into preβ, α, and preα-mobility particles, and can be separated by size in the range of from about 6 nanometers to about 12 nanometers. Specifically, lipoproteins are fractionated primarily with respect to differences in their electrophoretic mobility and/or size. When lipoproteins are fractionated using the electrophoretic technique, they are separated into the fractions of preβ-mobility HDL, α-mobility HDL, and preα-mobility HDL. A patient with CVD has less of α-1 HDL and α-2 HDL, and more of preβ-1 HDL. High levels of α-1 and α-2 are associated with low risk for CVD, while high level of preβ-1 HDL is associated with high risk for CVD. The results of HDL subpopulation analysis will allow the healthcare practitioner to more effectively treat patients with agents, such as various statin drugs and niacin, to normalize these particles and decrease CVD risk.

Apo A-I may be determined through immune-turbidimetric assay. The following information pertains to Apo A-I detection in patients and at risk levels:

Patient Preparation 8-12 hour fast prior to collection. Patient should preferably drink water only. Preferred Specimen 1.0 mL serum (0.5 mL minimum) collected in serum separator tube (SST/Tiger Top)

Alternate Specimen 1.0 mL EDTA plasma (0.5 mL minimum) collected in plasma separator tube (Pearl Top)

Transport Temperature: Refrigerated (ship on frozen cold packs)

Stability at Room Temperature: 1 day; Refrigerated: 8 days

Lab Values:

Male

Optimal: >160 mg/dL
Borderline: 120-160 mg/dL
High risk: <120 mg/dL

Female

Optimal: >180 mg/dL
Borderline: 140-180 mg/dL
High risk: <140 mg/dL

Clinical Significance: Low levels are associated with higher CVD risk.

Lipoprotein a Detection

Lp(a) is an LDL-like particle with a protein known as apo(a) attached to it. An elevated level of Lp(a) is an independent risk factor for heart attack and other cardiovascular diseases. Lipoprotein(a) or Lp(a) assay are standardized with the Apolipoprotein Standardization Program, Northwest Lipid Research Laboratory, University of Washington, Seattle, Wash., directed by Dr. Santica Marcovina. In studies with the Lipid Research Clinics Trial and the Framingham Offspring Study, the data indicate that the results of these assays are significant predictors of coronary heart disease (CHD), better than the standard LDL-C and HDL-C measurements (22-25). Moreover an Lp(a) assay may be isoform independent and provide good information about CHD risk. It may provide calculated values and ratios that have been found to very useful in CHD risk prediction: % of LDL-C as sdLDL-C, VLDL-C, non HDL-C, total cholesterol/HDL-C, apoB/apoA-I, VLDL-C/Triglyceride, and HDL-C/Triglyceride. Many healthcare providers have requested these ratios.

The term "lipoprotein (a)" or "Lp(a)", as used herein, refers to an LDL particle with another protein (referred to as apo(a)) attached thereto. A high value of this particle can interfere with the process of breaking up clots in a person's arteries. An Lp(a) value above 30 mg/dl is considered high, while a borderline value is between 20 mg/dl and 30 mg/dl, and an optimal value is below 20 mg/dl. A high value is associated with an increased risk of heart disease.

For example, LDL cholesterol may be measured using ultracentrifugation methods, electrophoresis methods, precipitation methods, methods that use polyethylene-glycol modified enzymes, methods that use synthetic polymers, immunological separation methods, and catalase reagent methods.

Ultracentrifugation for measuring LDL cholesterol separates lipoproteins based on their differing hydrated densities, which are adjusted by adding salts such as NaBr or KBr. Particularly, the proportion of lipid associated with the proteins for any one particular lipoprotein adds to the buoyancy of the lipoprotein complex, which allows it to be separated. Preparative fractionations are achieved by subjecting serum or plasma to ultracentrifugation at the native non-protein solute density, which floats TG-rich BLDL and chylomicrons. Those can be recovered using tube slicing or aspiration. The bottom fraction contains the LDL and HDL, which can be re-centrifuged, after adding salt, to float LDL.

For measuring of LDL-C by electrophoresis, lipoproteins may be separated using a variety of electrophoric media, such as paper, agarose gel, cellulose acetate, and polyacrylamide with one or more buffers. A preferred electrophoresis separation and immune-detection technique is described in co-owned and co-assigned U.S. Pat. No. 8,470,541, incorporated by reference. A common technique uses agarose gels to separate lipoproteins followed by precipitation with polyanions and densitometric scanning. This technique can be approved by the introduction of enzymatic cholesterol determination using cholesterol esterase, cholesterol dehydrogenase, and nitroblue tetrazolium chloride dye. An alternative technique uses agarose gel modified by addition of a cation such as magnesium, which slows migration of β and pre-β lipoproteins, producing a distinct additional band between pre-β and αlipoproteins, demonstrated to be Lp(a) by immunofixation. Addition of urea to the gel allows simultaneous quantification of the β, pre-β, and αfractions as well as Lp(a)-cholesterol with the mobility of Lp(a) independent of apo(a) size polymorphisms.

Lp(a) levels may be determined by immunoturbidimetric assay using the following method:

Patient Preparation: None
Preferred Specimen: 1.0 mL serum (0.5 mL minimum) collected in serum separator tube (SST/Tiger Top)
Alternate Specimen: 1.0 mL EDTA plasma (0.5 mL minimum) collected in plasma separator tube (Pearl Top)

Transport Temperature: Refrigerated (ship on frozen cold packs)

Stability when Refrigerated: 2 weeks

Lab Values:

Optimal: <20 mg/dL

Borderline: 20-30 mg/dL

High risk: >30 mg/dL

Clinical Significance: Elevated levels are an independent risk factor for myocardial infarction, coronary artery disease, cerebral vascular disease, vein graft stenosis and retinal artery occlusion.

SD LDL-C Level Detection

High blood levels of the cholesterol found in smaller, denser LDL (sdLDL-C) particles are associated with atherosclerosis—the build-up of fatty materials in arteries—increasing the risk for CVD events.

LDL subclasses are separated directly from plasma by non-equilibrium density-gradient ultracentrifugation using a six-step, curvilinear salt gradient. After centrifugation in a Beckman Optima XL100 ultracentrifuge [(2.02×105 g for 23 h) at 23° C.] in a swinging-bucket rotor (Beckman SW40Ti), the separated LDL subclasses are eluted from the tube by upward displacement through a micro-flow cell and detected by continuous spectrophotometric monitoring at 280 nm. The contents of the tube are collected into two pools: an initial pool of 2 ml containing the lighter, TG-rich lipoproteins (TGRL), followed by a 4 ml pool containing the total LDL. The lipoprotein content of these pools was established initially by collecting a large number of fractions across the density gradient and comparing the total protein concentration in these fractions (protein concentration profile) with the continuous-flow lipoprotein profile obtained at 280 nm. LDL subclasses are quantified by dividing proportionately the concentration of apo B in the 4 ml LDL pool on the basis of the relative percentage of each LDL subclass, as calculated from the relative percentage area beneath the profile of individual LDL subclasses. The areas beneath the LDL subclass curves are corrected for variations in the molar absorption coefficient at 280 nm across the lipoprotein profile, as described previously. The within-batch (within-rotor) and between-batch (between-rotor) coefficients of variation for the relative percentages of LDL subclasses are less than 6% and 6.5% respectively, as previously reported [20].

We report a method in which plasma may be adjusted to a density (D) of 1.044 and 1.060 g/ml, respectively, in two tubes, both of which may undergo ultracentrifugation (UC). A measure of SD-LDL apolipoprotein B (apo B) may be obtained by subtraction of the apo B concentration in D>1.060 g/ml lipoproteins from that in D>1.044 g/ml lipoproteins to correct for apo B associated with lipoprotein (a) [Lp(a)]. This procedure may be evaluated in paired plasma samples in healthy men (n=62) and in age-matched healthy women (n=74) and in age-matched primary dyslipidaemic men (n=72) and women (n=29) and compared with an established density-gradient ultracentrifugation (DGU) method.

An enzymatic assay can be used to quantify the amount of cholesterol in sdLDL particles which are denser and more atherogenic LDL-particles using the following method:

Patient Preparation: 8-12 hour fast prior to collection. Patient may drink water only.

Preferred Specimen: 1.0 mL serum (0.5 mL minimum) collected in serum separator tube (SST/Tiger Top)

Alternate Specimen: 1.0 mL EDTA plasma (0.5 mL minimum) collected in plasma separator tube (Pearl Top)

Transport Temperature: Refrigerated (ship on frozen cold packs)

Stability while Refrigerated: 3 days

Lab Values:

Optimal: <20 mg/dL

Borderline: 20-40 mg/dL

High risk: >40 mg/dL

Clinical Significance: High levels are associated with a 2- to 3-fold increased risk for CVD events and rate of arteriographic progression.

Methods of the invention may include the recommendation or administration of the following treatment options: diet; exercise and weight loss, if indicated; surgeries including stents, angioplasty, heart bypass surgery, valve disease treatment, cardioversion, enhanced external counter pulsation, ablation, or implantation of a pacemaker, an implantable cardioverter defibrillator, or a left ventricular assist device, or heart transplant; treatment with a drug such as ace inhibitors, angiotension II receptor blockers, antiarrhythmics, antiplatelet drugs, aspirin, beta-blocker therapy, statin therapy, calcium channel blocker drugs, clot buster drugs, digoxin, diuretics, nitrates, niacin, ezetimibe, fibrates, warfarin, or other blood thinners.

After selecting the appropriate parameters or biomarkers as described herein, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop the predictive algorithm. A selected population of individuals (i.e., a reference set or reference population) is used to train the algorithm, where historical information is available regarding the values of the selected parameters in the population and their clinical outcomes. To calculate a risk of developing a diabetic condition for a given individual, parameter values are obtained from one or more samples collected from the individual and/or from non-biological sources (i.e. completed questionnaires, etc.) obtained from the individual and used as input data (inputs into a predictive algorithm fitted to the actual historical data obtained from the selected population of individuals).

Any formula or algorithm may be used to combine selected parameter results into indices useful in the practice of the invention. As indicated above, and without limitation, such indices may indicate, among the various other indications, the probability, likelihood, absolute or relative risk, time to or rate of conversion from one disease state to another.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from selected parameter results in the relevant training population. Amongst other uses, such formula may be intended to map the feature space derived from one or more selected parameter inputs to a set of subject classes (e.g. useful in predicting class membership of subjects as normal, pre-Diabetes, Diabetes), to derive an estimation of a probability function of risk using a Bayesian approach (e.g. the risk of Diabetes), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. parameters) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., parameters/biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual selected parameter measurement into more valuable forms of information, prior to their presentation to the predictive formula. Most notably, normalization of parameter results, using either common mathematical transformations such as logarithmic or logistic functions, as normal or other distribution positions, in reference to a population's mean values, etc. are all well known to those skilled in the art. Of particular interest are a set of normalizations based on parameters not derived from biological samples such as age, gender, race, or sex, where specific formula are used solely on subjects within a class or continuously combining such a parameter as an input. In other cases, sample based parameters can be combined into calculated variables (much as BMI is a calculation using Height and Weight) which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean parameter values, according to the technique outlined in D'Agostino et al. (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves; and Vasan, R. S., 2006 regarding biomarkers of cardiovascular disease. In addition, the numeric result of a classifier formula itself may be transformed post-processing by its reference to an actual clinical population and study results and observed endpoints, in order to calibrate to absolute risk and provide confidence intervals for varying numeric results of the classifier or risk formula.

Parameter selection may involve utilizing a selection model to validate the representative population data set and selecting the parameter data from the data set that provides the most reproducible results. Examples of data set validation may include, but are not limited to, cross-validation and bootstrapping. From the parameter selection, the model to be used in evaluating a risk of developing a diabetic condition may be determined and selected. However, it is noted that not all models provide the same results with the same data set. For example, different models may utilize different numbers of parameters and produce different results, thereby adding significance to the combination of biomarkers on the selected model. Accordingly, multiple selection models may be chosen and utilized with the representative population data set, or subsets of the data set, in order to identify the optimal model for risk evaluation. Examples of the particular models, including statistical models, algorithms, etc., which may be used for selecting the parameters have been described above.

For each selection model used with the data set, or subset thereof, the parameters are selected based on each parameter's statistical significance in the model. When inputted into each model, the parameters are selected based on various criteria for statistical significance, and may further involve cumulative voting and weighting. Tests for statistical significance may include exit-tests and analysis of variance (ANOVA). The model may include classification models (e.g., LDA, logistic regression, SVM, RF, tree models, etc.) and survival models (e.g., cox), many examples of which have been described above.

It is noted that while parameters may be applied individually to each selection model to identify the statistically significant parameters, in some instances individual parameters alone may not be fully indicative of a risk for a diabetic condition, in which case combinations of parameters may be applied to the selection model. For example, rather than utilizing univariate parameter selection, multivariate parameter selection may be utilized. That is, a parameter may not be a good indicator when used as a univariate input to the selection model, but may be a good indicator when used in combination with other parameter (i.e., a multivariate input to the model), because each parameter may bring additional information to the combination that would not be indicative if taken alone.

Leading candidate models may be selected based on one or more performance criteria, examples of which have been described above. For example, from using the data set, or data subsets, with various models, not only are the models used to determine statistically significant parameters, but the results may be used to select the optimal models along with the parameters. As such, the evaluation model used to evaluate risk may include one of those used as a selection model, including classification models and survival models. Combinations of models markers, including marker subsets, may be compared and validated in subsets and individual data sets. The comparison and validation may be repeated many times to train and validate the model and to choose an appropriate model, which is then used as an evaluation model for evaluating risk of a diabetic condition.

In certain embodiments, a predictive multivariate model of CVD risk may include the following variables which may be determined from a patient sample (e.g., blood or plasma): an SdLDL-C level (mg/dL), a level of ApoA-1 in a-1 HDL (mg/dL), and a log(Lipoprotein(a)) level (mg/dL). Additionally, the model may include information from a patient history including age (years), smoker status (y/n), and use of blood pressure medication (y/n). These sets of values may be entered into a model that includes a pre-determined set of coefficients. The model may then transform the patient levels and information into a CVD hazard factor indicative of the patient's risk of developing CVD. The CVD hazard factor may be further transformed into a probability (p) score represented as $p=1/(1+e^{(-x)})$ where x is the CVD hazard factor. In certain embodiments, a patient report may indicate that a patient is at high risk of developing CVD where p is greater than 10%, 20%, 30%, 40%, 50%, 60%, 70%, 80%, or 90%, for example.

Any development environment or language known in the art may be used to implement embodiments of the invention. Exemplary languages, systems, and development environments include Perl, C++, Python, Ruby on Rails, JAVA, Groovy, Grails, Visual Basic .NET. An overview of resources useful in the invention is presented in Barnes (Ed.), Bioinformatics for Geneticists: A Bioinformatics Primer for the Analysis of Genetic Data, Wiley, Chichester, West Sussex, England (2007) and Dudley and Butte, A quick guide for developing effective bioinformatics programming skills, PLoS Comput Biol 5(12):e1000589 (2009).

In some embodiments, methods are implemented by a computer application developed in Perl (e.g., optionally using BioPerl). See Tisdall, Mastering Perl for Bioinformatics, O'Reilly & Associates, Inc., Sebastopol, CA 2003. In some embodiments, applications are developed using BioPerl, a collection of Perl modules that allows for object-oriented development of bioinformatics applications. BioPerl is available for download from the website of the Comprehensive Perl Archive Network (CPAN). See also Dwyer, Genomic Perl, Cambridge University Press (2003) and Zak, CGI/Perl, 1st Edition, Thomson Learning (2002).

In certain embodiments, applications are developed using Java and optionally the BioJava collection of objects, developed at EBI/Sanger in 1998 by Matthew Pocock and Thomas Down. BioJava provides an application programming interface (API) and is discussed in Holland, et al., BioJava: an open-source framework for bioinformatics, Bioinformatics 24(18):2096-2097 (2008). Programming in Java is discussed in Liang, Introduction to Java Programming, Comprehensive (8th Edition), Prentice Hall, Upper Saddle River, N.J. (2011) and in Poo, et al., Object-Oriented Programming and Java, Springer Singapore, Singapore, 322 p. (2008). Applications can be developed using the Ruby programming language and optionally BioRuby, Ruby on Rails, or a combination thereof. Ruby or BioRuby can be implemented in Linux, Mac OS X, and Windows as well as, with J Ruby, on the Java Virtual Machine, and supports object oriented development. See Metz, Practical Object-Oriented Design in Ruby: An Agile Primer, Addison-Wesley (2012) and Goto, et al., BioRuby: bioinformatics software for the Ruby programming language, Bioinformatics 26(20): 2617-2619 (2010).

Systems and methods of the invention can be developed using the Groovy programming language and the web development framework Grails. Grails is an open source model-view-controller (MVC) web framework and development platform that provides domain classes that carry application data for display by the view. Grails domain classes can generate the underlying database schema. Grails provides a development platform for applications including web applications, as well as a database and an object relational mapping framework called Grails Object Relational Mapping (GORM). The GORM can map objects to relational databases and represent relationships between those objects. GORM relies on the Hibernate object-relational persistence framework to map complex domain classes to relational database tables. Grails further includes the Jetty web container and server and a web page layout framework (SiteMesh) to create web components. Groovy and Grails are discussed in Judd, et al., Beginning Groovy and Grails, Apress, Berkeley, Calif., 414 p. (2008); Brown, The Definitive Guide to Grails, Apress, Berkeley, Calif., 618 p. (2009).

Figure 2:
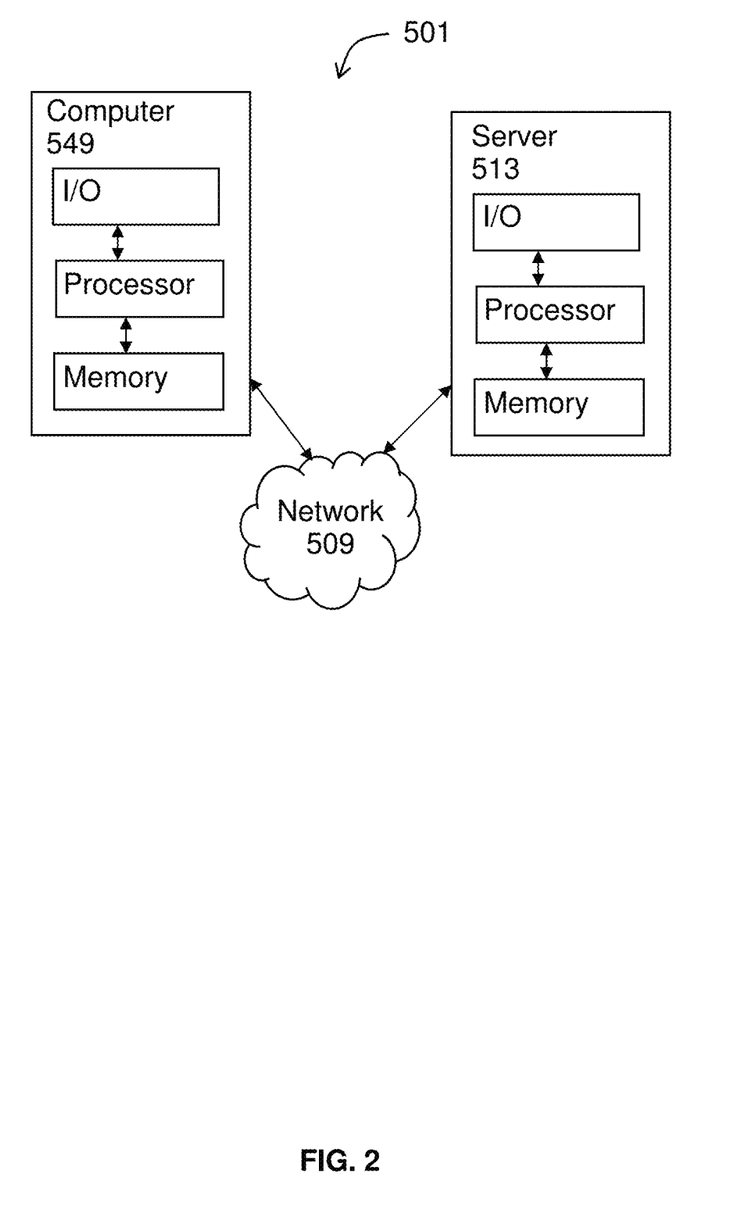
FIG. 2 illustrates a system of the invention.

Methods described herein can be performed using a system that includes hardware as well as software and optionally firmware. For example, a system 501 of the invention may include a computer 549 including an input/output device (I/O), coupled to a processor and a non-transient, tangible memory. The computer may be in communication with other computers or a server 513 through a network 509. A computer such as a personal computing device (e.g., a laptop, desktop, tablet) may be used to implement embodiments of the invention. In general, a computer includes a processor coupled to memory and at least one input/output device.

A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

Memory generally includes a tangible, non-transitory computer-readable storage device and can include any machine-readable medium or media on or in which is stored instructions (one or more software applications), data, or both. The instructions, when executed, can implement any or all of the functionality described herein. The term "computer-readable storage device" shall be taken to include, without limit, one or more disk drives, tape drives, flash drives, solid stated drives (SSD), memory devices (such as RAM, ROM, EPROM, etc.), optical storage devices, and/or any other non-transitory and tangible storage medium or media.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

In various embodiments, systems and methods of the invention may include the generation of a report. Such reports may be digital or physical. Reports may include information regarding a patient's CVD risk and may be produced by a computer and sent to an output device such as a monitor or a printer. In certain embodiments a digital report may be sent via an NIC or other output device to a medical provider or directly to a patient through digital communication methods such as e-mail. In certain aspects, a report may be stored on one or more computers or servers and accessed by the patient, the patient's medical provider, or other individuals via an online portal or website for viewing on or downloading to that individual's computer. In certain embodiments, reports may include CVD risk evaluations according to the invention performed at multiple time points for one or more individuals so that disease or disease risk progression may be observed over time or compared to an individualized baseline for an individual patient or patient population based on their early or first measured CVD hazard factor or CVD risk profile.

EXAMPLES

Example 1

Reference Set

A reference set of 2,620 men and women with a mean age of 58 years were followed for 8.5 years. A number of parameters were evaluated among the converters (those who developed CVD within the study period) and non-converters (those who did not develop CVD within the study period), C reactive protein (CRP), high density lipoprotein cholesterol (HDL-C), triglycerides, total cholesterol, direct low density lipoprotein cholesterol (LDL-C), small dense LDL-C(sdLDL-C), lipoprotein(a), and apolipoprotein (apo) A-I content of HDL particles as separated by two dimensional gel electrophoresis. Blood pressure, body mass index, waist circumference, history of diabetes, and use of blood pressure, cholesterol, and glucose lowering medications was also assessed. Follow-up information including CVD status over a median of 12.3 years was available for 1,083 men, mean age 59 years and without CVD at onset, of whom 207 (19.1%) developed CVD. A model was developed to predict new onset CVD using only those variables that provided significant information in a stepwise logistic regression analysis to calculate the area under the curve (AROC) and C statistic.

The parameters selected above were then evaluated using stepwise regression analysis. SAS LOGISTIC Procedure was used to perform the analysis. It was determined that the following variables provided an overall C statistic of 0.73: 1. age, 2. blood pressure treatment, 3. Lp(a), 4. sdLDL-C, 5. ApoA-I in large α-1 HDL, 6. smoking, and 7. diabetes. This model was significantly superior to a model using the standard risk factors or one also using CRP (C statistic 0.68).

Example 2

Complete follow-up information including new onset heart disease, stroke or peripheral vascular disease (CVD) over a median of 12.3 years was available for 2,416 men and women, mean age 58 years, all of whom had no CVD at onset of the study.

Of these subjects, 336 developed CVD over the course of the study. Broken down by gender, 207 men (19.1%) and 129 women (9.7%) developed new onset documented CVD. Parameters found to predict CVD in men are shown in table 1 below.

| Parameter | Controls | Cases | % Difference |
|---|---|---|---|
| Age (years) | 57.2 | 63.1 | +10.3**** |
| Treated BP (%) | 23.0 | 43.6 | +190.0**** |
| Lipoprotein(a) (mg/dL) | 21.5 | 24.6 | +14.5*** |
| Sd LDL-C (mg/dL) | 31.4 | 36.4 | +16.0** |
| ApoA-I in α-1 HDL (mg/dL) | 14.9 | 12.7 | −14.5** |
| Diabetes (%) | 9.7 | 17.0 | +175* |
| Current Smoking (%) | 14.2 | 16.9 | +19.0* |

****$p < 0.0001$,
***$p < 0.001$,
**$p < 0.01$,
*$p < 0.05$,
C statistic 0.734

The following variables entered the model and provided an overall C statistic of 0.734:
1. Age
2. Treated high blood pressure
3. Lipoprotein(a) with log transf.
4. Small dense LDL-C
5. ApoA-I in very large α-1 HDL
6. Diabetes
7. Smoking (within the past year)

The above characteristics, tailored to the data of the study, can provide a multivariate model with the ability to predict CVD using LDL & HDL particles, and Lp(a) that is superior to standard risk prediction methods (C statistic 0.73 vs. 0.68, sdLDL-C better than TC, nonHDL-C, or LDL-C, and apoA-I in large HDL better than HDL-C).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:
1. A method for assessing cardiovascular risk, the method comprising the steps of:
  obtaining a sample from a patient;
  conducting an assay on the sample to determine blood levels of sdLDL-C, ApoA1 in α-1 HDL, and Lp(a);
  obtaining information about the patient's age and history of blood pressure treatment, smoking, and diabetes; and determining a probability of the individual developing cardiovascular disease based on the determined blood levels and the obtained information.

2. The method of claim 1, wherein the assay comprises one selected from the group consisting of an enzymatic assay, high-performance liquid chromatography, affinity chromatography, an immunoassay, a radioassay, an enzyme-linked immunosorbent assay, colorimetry, and an electrochemical assay.

3. The method of claim 1, further comprising administering a therapy to the patient based on the determined probability of the individual developing cardiovascular disease.

4. The method of claim 3, wherein administering the therapy comprises administering a statin drug.

5. The method of claim 1, further comprising producing a report describing the cardiovascular risk for the patient.

* * * * *